United States Patent [19]

Gosling et al.

[11] 4,359,456

[45] Nov. 16, 1982

[54] ANTIPERSPIRANT ACTIVITY OF BASIC ALUMINUM COMPOUNDS

[75] Inventors: Keith Gosling, Richmond; Nigel L. Jackson, Otley; Nicholas H. Leon, Isleworth; Victor J. Mulley, Reading; Michael J. Baldock, Isleworth, all of England

[73] Assignee: Lever Brothers Company, New York, N.Y.

[21] Appl. No.: 213,450

[22] Filed: Dec. 5, 1980

Related U.S. Application Data

[63] Continuation of Ser. No. 51,523, Jun. 25, 1979, abandoned, which is a continuation-in-part of Ser. No. 910,988, May 30, 1978, abandoned, which is a continuation of Ser. No. 758,834, Jan. 12, 1977, abandoned.

[30] Foreign Application Priority Data

Jan. 14, 1976 [GB] United Kingdom ............... 1401/76
Jun. 23, 1978 [GB] United Kingdom ............. 27755/78

[51] Int. Cl.³ ............................................. C01F 7/48
[52] U.S. Cl. ...................................... 424/68; 423/462
[58] Field of Search .................. 423/462, 495; 424/68; 252/313 R, 314, 317

[56] References Cited

U.S. PATENT DOCUMENTS 3,544,476 12/1970 Aiba ..................................... 423/495
3,904,741  9/1975 Jones ................................... 423/462

FOREIGN PATENT DOCUMENTS 1041933 10/1958 Fed. Rep. of Germany ...... 423/462
2630768  1/1977 Fed. Rep. of Germany ...... 423/462
51-41600 11/1976 Japan ................................... 423/462
 621672  4/1949 United Kingdom ................ 423/462
1460966  1/1977 United Kingdom ................ 423/462
1525082  9/1978 United Kingdom .
2048229 12/1980 United Kingdom ................ 423/462

OTHER PUBLICATIONS

Partial Translation of Japanese Patent Specification 51-41600/1976.
"Effects of Topically Applied Agents on the Eccrine Sweat Glands", *Advances in Modern Technology*, vol. 4, (1976), pp. 18-23.
*Izvestiya Akademii Nauk Larvinskoi SSR, Seriya Kimicheskaya*, pp. 421-426, No. 4, (1973), (translation relied on).

*Primary Examiner*—Brian E. Hearn
*Attorney, Agent, or Firm*—Feit, Irving N.; James J. Farrell

[57] ABSTRACT

An improved antiperspirant active material, and methods for its preparation, identification and use as well as cosmetic compositions containing said material are disclosed. Said material comprises a polymeric aluminum compound having the empirical formula $$Al_2(OH)_{6-a}X_a$$

where X is Cl, Br or I, a is about 0.3 to about 4; wherein said antiperspirant active material is further characterized by:
  (a) a Size Exclusion Chromatography Test band having a relative retention time corresponding to Band III of the Standard Basic Aluminum Chloride Solution Size Exclusion Chromatogram; and
  (b) a Band III Percent Aluminum Value of at least 20 percent.

9 Claims, No Drawings

ANTIPERSPIRANT ACTIVITY OF BASIC ALUMINUM COMPOUNDS

This Application is a continuation of Ser. No. 051,523 filed June 25, 1979 which is continuation in part of Ser. No. 910,988 filed May 30, 1978 which was a continuation of Ser. No. 758,834 filed Jan. 12, 1977 all now abandoned.

INTRODUCTION

This Application is a continuation-in-part Application to Ser. No. 910,988 filed May 30, 1978 which was a continuation of Ser. No. 758,834 filed Jan. 12, 1977 all now abandoned. In the aforecited parent Application there was described basic aluminium chloride, bromide, iodide and nitrate compounds having enhanced antiperspirant activity. Although basic aluminium compounds are well known to have antiperspirant activity it was disclosed in the parent Application that an enhancement in the antiperspirant activity of basic aluminium compounds can be obtained under certain conditions of prolonged heating in aqueous solution. Heretofore Applicants have noted that this enhanced effectiveness was closely related to the formation of a higher polymeric species having a size of above 100 Angstroms. In particular the antiperspirant active compounds having enhanced activity were defined in said parent Application as those which in water, form an aqueous solution, in which there is at least 2% by weight of the total aluminium contained in polymeric species having a size greater than 100 Angstroms.

Applicants have now made a further discovery concerning the characterisation of basic aluminium chloride, bromide and iodide compounds which have enhanced antiperspirant activity and in particular that said enhanced activity does not depend on the requirement that their aforementioned aqueous solution must contain at least 2% by weight of the aluminium contained in polymers exceeding 100 Angstroms in effective diameter, and indeed they may in aqueous solution contain substantially no polymers of such size.

Applicants have now found that their improved antiperspirant active material comprises a polymeric aluminium compound having the empirical formula

$Al_2(OH)_{6-a}X_a$ where X is Cl, Br or I, a is about 0.3 to about 4 and wherein said antiperspirant active material may or may not contain polymers exceeding 100 Angstroms in effective diameter but are characterized by
 (a) a Size Exclusion Chromatography Test Band having a relative retention time corresponding to Band III of the Standard Basic Aluminium Chloride Size Exclusion Chromatogram; and
 (b) a Band III Percent Aluminium Value of at least 20 percent.

These terms will be defined in detail in the specification to follow. This latest discovery in the characterisation of the enhanced species has been disclosed in British Patent Application No. 27755/78 filed June 23, 1978 to which Applicants also claim priority.

STATE OF THE ART

For inhibiting perspiration, the application to the skin of many different antiperspirant active compounds has been described in the literature. However, those compounds most widely used in commercial products at the present time are basic aluminium halides, especially aluminium chlorhydrate, which has an Al/Cl molar ratio of about 2. These active compounds are applied to the skin from a variety of applicator types including aerosol sprays, pump sprays, squeeze packs, roll-ons and stick applicators. Thus aluminium chlorhydrate, for example, is employed as the active ingredient of various liquid, cream, stick or dry powder antiperspirant compositions. However, in spite of the popularity of aluminium chlorhydrate the presently available products are capable of producing only limited reduction in perspiration.

In Izvestiya Akademii Nauk Latvinskoi SSR, Seriya Khimicheskaya, No. 4 (1973) 421–426, there is described an investigation into the effect of the time and the temperature of heating and the concentration of solutions of aluminium chlorhydrate $Al_2(OH)_5Cl$ on the preparation of boehmite. It is reported that boehmite is formed when aluminium chlorhydrate solutions with an aluminium ion concentration of 6.1 to 48.6 mg/ml are heated at 160° C. for 5 hours under hydrothermal conditions. When the aluminium ion concentration is 64.8 mg/ml or higher it is reported that no boehmite is formed as indicated by X-ray crystallography or differential thermal analysis. Furthermore, results are given of a study of the effect of temperature on the heating of aluminium chlorhydrate solutions with an initial $Al^{3+}$ concentration of 8.1 and 16.2 mg/ml in which study solutions were heated for 5 hours at 100°, 120°, 140°, 160° and 180° C. in sealed ampoules. At 100° and 120° C. the samples did not exhibit the characteristic reflections of boehmite in the X-ray diffraction diagrams.

DEFINITION OF TERMS

Certain terms, standards and tests to be employed by the Applicants in the course of their disclosure of their invention will be unique to their application and as yet may not be readily known in the antiperspirant art. Accordingly Applicants set forth the following definition that will facilitate the understanding of their disclosure.

I STANDARD BASIC ALUMINIUM CHLORIDE SOLUTION

As will be seen below the measure of the species that provide the enhanced antiperspirant effectiveness will be related to the presence of a particular band detected in the Size Exclusion Chromatography test which will be defined below. This band has a particular relative retention time that may be related to a corresponding band present in a Standard Basic Aluminium Chloride Solution which is prepared as follows:

The Standard Basic Aluminium Chloride Solution is prepared having an aluminium concentration of 12.5% by weight from 19.1 g of aluminium chloride hexahydrate, 10.5 g of 99.9% pure aluminium wire (0.76 mm diameter, cut in approximately 1 cm lengths and degreased by washing in acetone) and 70.4 g of deionized water. The mixture is stirred and heated at 80°–90° C. under a reflux condenser until all of the aluminium is dissolved. Any traces of insoluble solids are removed by filtration to give a clear solution.

II SIZE EXCLUSION CHROMATOGRAPHY TEST

The Size Exclusion Chromatography test is an analytical technique related to High Performance Liquid Chromatography.

The analytical procedure is performed on a stainless steel column of dimensions 30 cm high and of 7 mm internal diameter packed with porous silica of nominal particle size 5 microns and pore size of 60 Angstroms, which silica has been deactivated by silylation to eliminate adsorption in size exclusion separations. In particular packing employed is a material supplied by the Merck Corporation of Darmstandt, Germany under the trademark of LiChrosorb RP-2. The packing in addition to the characterisations above has a cumulative undersize particle size distribution by weight of 10% less than 5 microns, 50% less than 6 microns and 90% less than 7 microns.

The column is fitted at the bottom with a zero dead volume fitting containing a 2 micron mesh stainless steel bed support. The silica is packed into the column by the high pressure slurry method (see Practical High Performance Liquid Chromatography, Edited by C. F. Simpson, 1976, Appendix II), using methanol:water (90:10) containing 1% sodium acetate as the packing medium.

After packing, the column is capped with another zero dead volume fitting containing a 2 micron stainless steel mesh. The packed column is then eluted with 200 ml of methanol at a flow rate of about 10 ml/min, using a high pressure pump, to consolidate the bed and wash out the packing medium. The bed is topped up, if necessary, with a thick slurry of the packing in methanol followed by reconsolidation.

A differential refractive index monitor (e.g. Waters R401) is used to detect sample fractions as they are eluted. It is linked to a pen recorder to provide a chromatogram and to an integrator (e.g. Infotronics CRS 309) which measures the elution times of the fractions and the relative chromatographic band areas. The integrator is required to measure areas of bands not resolved to the baseline by dropping perpendiculars from the lowest point of the valleys separating the bands to the baseline.

The column packing should be tested according to the procedure of Bristow & Knox (Chromatographia, Volume 10, No. 6, June 1977, pp 279–88) for reverse phase materials and should generate at least 20,000 plates/meter for the test component phenetole.

To prepare test solutions of the materials for analysis by the Size Exclusion Chromatography Test those already in solution are diluted, if necessary, with deionized water to give 2 g of a solution containing 2.5% by weight aluminium and dispersed by treatment with a sonic probe for 2 minutes. The solutions prepared in this way are filtered through a 25 mm diameter membrane having a pore size of 0.025 micrometers to give the test solutions. The preparation of a test solution should be carried out immediately prior to application of a sample thereof to the column.

Samples containing about 4 micromoles of aluminium are applied to the top of the column by means of a precision microliter syringe and a sample injection port. The sample is eluted with a $1 \times 10^{-2}$ M aqueous nitric acid solution at a flow rate of 1.0 ml/min using a high pressure pump. The eluent is maintained at a temperature of 22°–23° C.

Eluted fractions of a test sample are characterized by means of the ratio of their retention times to that of the totally included species which in the case of basic aluminium chlorides is due to hydrochloric acid (which is present in solutions of basic aluminium chlorides) as shown by comparison of its retention time with that of a sample of hydrochloric acid.

III BANDS I, II, III AND IV OF THE STANDARD BASIC ALUMINIUM SIZE EXCLUSION CHROMATOGRAM

Employing the above techniques on a standard solution of a basic aluminium chloride prepared as described above, Applicants have obtained a separation of four aluminium-containing fractions having relative retention times within the ranges indicated and with typical relative retention times and chromatographic band areas expressed as percentages of the total chromatographic band area representing aluminium-containing material as also indicated below.

|  | Band I | Band II | Band III | Band IV |
| --- | --- | --- | --- | --- |
| Relative Retention Time Range | 0.62–0.70 | 0.71–0.75 | 0.76–0.82 | 0.83–0.97 |
| Typical Relative Rention Time | 0.65 | 0.73 | 0.79 | 0.91 |
| Band Area % of total aluminium band area | 39 | 51 | 4 | 6 |

The standard solution contained 0% aluminium as polymers greater than 100 Angstroms in effective diameter.

It will be appreciated by those skilled in the art that mechanisms of separation other than the principal mechanism of size exclusion may play a part in this type of chromatography. Examples of the processes would be adsorption effects and hydrodynamic effects. Thus although it is possible for a given column and constant operating conditions to lead to invariable relative retention times, minor variations in particle size range and pore size distribution of the column packing material may lead to slight differences in relative retention times.

IV DETERMINATION OF PERCENTAGE ALUMINIUM IN POLYMERIC SPECIES HAVING A SIZE GREATER THAN 100 ANGSTROMS

For this purpose there was used a 1.2 m×6.0 mm column packed with sperical porous silica beads of particle size 75–125 microns, and of surface area 350–500 m²/g, and having a maximum pore size of 100 Angstroms. The silica employed, available commercially as Porasil AX, had been deactivated to eliminate adsorption in molecular size separations. The use of Porasil silica beads as a column packing in chromatography is referred to in "Gel Permeation Chromatography" by K. H. Altgelt and L. Segal, 1971, pages 16–18. The silica was conditioned before use by passage of a single large sample (e.g. 0.2 ml of a 5% w/w solution) of a heat-treated aluminium chlorhydrate. Samples to be tested were made up in deionized water to approximately 0.2 M aluminium and thoroughly dispersed by treatment (4 minutes) with a sonic probe. About 0.2 ml samples of approximately 0.2 M aluminium solutions were applied to the column by a sample loop system and eluted with $10^{-2}$ M aqueous nitric acid solution using a peristaltic pump. A differential refractive index monitor linked to a pen recorder was used to detect fractions as they were eluted. These fractions were collected and analysed for aluminium by atomic adsorption. Complete elution of all aluminium applied in each sample was checked by direct analysis of another sample of the same volume. The percentage of the total aluminium which appeared in the fraction eluted at the void volume of the column was considered as that deriving from polymeric material of a size greater than 100 Angstroms in effective diameter.

V BAND III PERCENT ALUMINIUM VALUE

Quantitatively, the amount of aluminium in the Band III fraction expressed as a percentage of the total aluminium of the compound under test is readily determined from the area of its band on the chromatogram. This percentage is derived from the expression $$\% \text{ Aluminium} = (100 - A) \times \frac{\text{Area of band corresponding to Band III fraction}}{\text{Sum of the areas of the bands corresponding to the aluminium-containing fractions}}$$

where A is the weight percentage of the total aluminium which is contained in polymers greater than 100 Angstroms.

In experiments performed by the Applicants using certain samples of test materials, the complete elution of all the applied aluminium in a sample was checked by direct analysis of another sample of the same volume by plasma emission spectrophotometry. The correlation between band area percentage and aluminium percentage was also verified by direct analysis. The fractions were collected as they emerged from the refractive index monitor and their individual aluminium contents measured also by plasma emission spectrophotometry.

VI BAND III PERCENT ALUMINIUM VALUES OF COMMERCIAL MATERIALS

The Applicants have analysed samples of a number of commercially available aluminium chlorhydrates recommended for use as antiperspirant agents. The percentage of aluminium in the Band III fraction for the tested samples is indicated below.

|  | % Aluminium in Band III Fraction |
|---|---|
| 50% aqueous solution of aluminium chlorhydrate[1] | 6 |
| 50% aqueous solution of aluminium chlorhydrate[2] | 2 |
| Dried powder of aluminium chlorhydrate[3] | 8 |
| Dried powder of aluminium chlorhydrate[4] | 4 |
| Spray dried powder of aluminium chlorhydrate[5] | 10 |

[1]From Armour Pharmaceutical (Ireland) Limited as "Reheis Chlorhydrol".
[2]From Albright & Wilson.
[3]From Hoechst AG as Locron P.
[4]From Hoechst AG as Locron P extra.
[5]From Armour Pharmaceutical (Ireland) Limited as "Reheis aluminium chlorhydrate Microdry Ultrafine".

DETAILED DESCRIPTION OF THE INVENTION

We have discovered that by modifying basic aluminium compounds having the empirical formula:

$$Al_2(OH)_{6-a}X_a$$

wherein X is Cl, Br or I and a is about 0.3 to about 4 so as to increase the aluminium content of the Band III fraction thereof, the antiperspirant activity thereof is enhanced.

Such increase in activity may be brought about by heating aqueous solutions of the basic aluminium compound in the same way as described in the parent Application referred to above and as will be set forth below. While enhancement of the percentage of aluminium in the Band III fraction in many cases is accompanied by the production of polymeric species having an effective diameter above 100 Angstroms in which species a substantial proportion of the aluminium may be contained, we have found that this is not necessarily so. The present application is therefore more particularly concerned with the enhancement of antiperspirant efficacy by treatment conditions which may or may not result in 2% or more of the aluminium being present in polymers having a size greater than 100 Angstroms. In particular the increased efficacy is now characterized by the fact that in the size exclusion chromatographic procedure described herein there is eluted a fraction between the relative retention times of 0.76 and 0.82 in which fraction there is contained at least 20% of the total aluminium of the compound. For convenience, such fraction is referred to hereinafter as the Band III fraction.

The amount of aluminium contained in the Band III fraction is preferably at least 25%, more preferably at least 30%, and may even exceed 80%, of the total aluminium.

The above-described special forms of basic aluminium compounds may be prepared by heating aqueous solutions of the basic aluminium compounds at elevated temperature, as more particularly described herein. The production of the desired species depends on the appropriate choice of the reaction conditions which are interrelated. It is preferred to use temperatures of from 50° C. to 140° C. The period of heating may be shorter as higher temperatures are used, ranging for example from 0.5 hour to 30 days. Of importance is the concentration of the basic aluminium compound. The aluminium concentration of the solution of the basic aluminium compound to be treated may range from 2.5% to 8.5% by weight, preferably from 3 to 6.5% by weight. While low temperatures such as 50° C. favour production of a product containing Band III polymers without any polymers above 100 Angstroms, the rate of production of the polymeric species present in the Band III fraction is lower. Therefore, higher temperatures, up to about 140° C. are preferable, and production of polymers above 100 Angstroms may, if desired, be prevented or minimised by appropriate choice of the Al:Cl, Br or I molar ratio and solution concentration. The time for which the treatment is carried out should be sufficient to produce a substantial enhancement of the Band III fraction.

The conditions of heat treatment described herein have been found to give rise to the improved basic aluminium compound in amorphous form, and in particular the formation of boehmite, as determined by X-ray diffraction, has not been observed. The production of a substantial amount of boehmite or other crystalline forms of alumina would be considered to be disadvantageous.

According to the invention a preferred process for making an aqueous solution of an antiperspirant compound comprises heating an aqueous solution of a compound of the empirical formula:

$$Al_2(OH)_{6-a}X_a$$

where X is Cl, Br or I and a is from 0.3 to 4, preferably 0.8 to 2.0, said solution having an aluminium concentration of from 2.5 to 8.5% by weight, at a temperature of from about 50° C. to about 140° C. for a time sufficient to give rise in said solution to Band III polymeric species having a Band III Percent Aluminium Value of at least 20 percent.

The aqueous solution of the more active antiperspirant compound comprising the Band III polymeric species as defined, may, if desired, be dried to give the compound in the form of a solid hydrate. As with untreated aluminium chlorhydrate, for example, drying conditions which lead to both the loss of water of condensation, between the hydroxy groups of the compound, and hydrochloric acid should be avoided as these may lead to irreversible degradation of the treated basic aluminium compound. Any suitable method of drying may be used, spray drying being a particularly useful method. The spray drying method described in U.S. Pat. No. 3,887,692 may be employed. The solid material may be ground or milled as required.

Accordingly a preferred method of making an improved solid hydrated antiperspirant active compound comprises spray drying an aqueous solution of a basic aluminium chloride, bromide or iodide wherein said solution contains Band III polymeric species and having a Band III Percent Aluminium Value of at least 20 percent to produce a solid hydrate having a Band III Percent Aluminium Value of at least 20 percent.

The above processes are preferably conducted in such manner that within said Band III species there is contained from at least 25% of the total aluminium. More preferably there is contained 30% of the total aluminium.

Specifically provided by the instant invention is a method of inhibiting perspiration comprising applying to the skin an amount, sufficient to inhibit perspiration, of an antiperspirant active material comprising a polymeric aluminium compound having the empirical formula:

$$Al_2(OH)_{6-a}X_a$$

where X is Cl, Br or I and a is about 0.3 to about 4, and wherein said antiperspirant active material is further characterized by:
(a) having a Size Exclusion Chromatography Test Band having a relative retention time corresponding to Band III of the Standard Basic Aluminium Chloride Solution Size Exclusion Chromatogram; and
(b) having a Band III Percent Aluminium Value of at least 20 percent.

The compound may be applied to the skin as a powder or as a solution containing from 2.5% by weight aluminium. Solution containing lower concentrations of the basic aluminium compound have less antiperspirant effectiveness and in any case are not capable of being characterized by the Band III Percentage Aluminium Value since the test method herein for determining this requires use of a solution having an aluminium concentration of 2.5% by weight.

Further provided by the instant invention is a package consisting of the combination of an antiperspirant active polymeric aluminium compound and an applicator for applying the compound to the skin, wherein the polymeric aluminium compound has the empirical formula:

$$Al_2(OH)_{6-a}X_a$$

where X is Cl, Br or I and a is about 0.3 to about 4 and said formula including in the case of the said aluminium compound in solid form about 0.5 to about 8 molecules of water of hydration, and wherein said antiperspirant active material is further characterized by:
(a) having a Size Exclusion Chromatography Test Band having a relative retention time corresponding to Band III of the Standard Basic Aluminium Chloride Solution Size Exclusion Chromatogram; and
(b) having a Band III Percent Aluminium Value of at least 20 percent.

Also provided for by the instant invention is a cosmetic antiperspirant composition comprising:
(A) an amount sufficient to inhibit perspiration of a powdered antiperspirant active material in;
(B) a cosmetically acceptable base selected from the group consisting of powdered inert solid diluents and organic liquid carriers, wherein said antiperspirant active material comprises a polymeric aluminium compound having the empirical formula:

$$Al_2(OH)_{6-a}X_a\cdot nH_2O$$

where X is Cl, Br or I, a is about 0.3 to about 4 and n is about 0.5 to about 8, wherein said antiperspirant active material is further characterized by:
(a) having a Size Exclusion Chromatography Test Band having a relative retention time corresponding to Band III of the Standard Basic Aluminium Chloride Solution Size Exclusion Chromatogram; and
(b) having a Band III Percent Aluminium Value of at least 20 percent.

Additionally provided by the instant invention is a cosmetic antiperspirant composition comprising:
(A) an amount sufficient to inhibit perspiration of an antiperspirant active material in aqueous solution having an aluminium concentration of at least 2.5% by weight in combination with;
(B) a cosmetically acceptable adjunct selected from the group consisting of a perfume, thickener, alcohol and propellant,
wherein said antiperspirant active material comprises a polymeric aluminium compound having the empirical formula:

$$Al_2(OH)_{6-a}X_a$$

where X is Cl, Br or I and a is about 0.3 to about 4, and wherein said antiperspirant active material is further characterized by:
(a) having a Size Exclusion Chromatography Test Band having a relative retention time corresponding to Band III of the Standard Basic Aluminium Chloride Solution Size Exclusion Chromatogram; and (b) having a Band III Percent Aluminium Value of at least 20 percent.

In accordance with another aspect of the invention there is provided an antiperspirant composition comprising an aqueous solution of an antiperspirant active compound in combination with an adjunct which is a perfume, thickener, alcohol or propellant. The antiperspirant composition may be in the form of a lotion comprising an aqueous or aqueous alcoholic solution of the basic aluminium compound having an aluminium concentration of from 2.5 to 8.5% by weight and 0.1 to 5% by weight of a thickening agent. Suitable thickening agents for antiperspirant lotions are well known to those skilled in the art, and include for example, magnesium aluminium silicates. Thickening may also be effected by emulsifying an oil or the like in the composition. Furthermore, the composition may comprise an aqueous or aqueous alcoholic solution of the basic aluminium compound having an aluminium concentration of from 2.5% to 8.5% by weight and from 0.1 to 1% by weight of perfume.

The composition may comprise an aqueous alcoholic solution of the basic aluminium compound containing from 1 to 60% by weight of an alcohol. These aqueous alcoholic compositions preferably contain ethanol or isopropanol as the alcohol which are preferably present in an amount of from about 1% to about 30% by weight of the composition. Antiperspirant compositions comprising an aqueous solution of the active compound may contain from about 1 to 80% by weight of a propellant.

The antiperspirant composition may also comprise in combination a powdered antiperspirant active compound and a powdered inert solid diluent or organic liquid carrier. The composition may be in the form of a powder aerosol composition comprising a suspension of the basic aluminium compound in particulate form in a liquid carrier, said composition also comprising a propellant. In particular the composition may be in the form of a powder aerosol comprising:

A. from about 1% to about 12% by weight of said basic aluminium compound in powder form;
B. from about 0.1% to about 5% by weight of a suspending agent;
c. from about 1% to about 15% by weight of a carrier liquid; and
D. from about 70% to about 96% by weight of a propellant.

The carrier liquid may for example be a non-volatile non-hygroscopic liquid as suggested in U.S. Pat. No. 3,968,203. Especially useful are carrier liquids which have emollient properties and a number of these are referred to in British Patent Specification No. 1,393,860. Especially preferred are fatty acid esters such as isopropyl myristate and those esters referred to in British Patent Specification No. 1,353,914 such as dibutyl phthalate and diisopropyl adipate.

Various other carrier liquids for powder suspension aerosols are suggested in U.S. Pat. Nos. 3,833,721, 3,833,720, 3,920,807, 3,949,066 and 3,974,270, and in British Patent Specifications Nos. 1,341,748, 1,300,260, 1,369,872 and 1,411,547. Volatile carrier liquids may also be used such as ethanol as described in South African Patent Specification No. 75/3576, and volatile silicones.

The ratio of total solids in the compositions to the carrier liquid may vary over a wide range, for example from 0.01 to 3 parts of the powder per part by weight of the carrier liquid.

The propellant can be a liquefied hydrocarbon, halogenated hydrocarbon or a mixture thereof. Examples of materials that are suitable for use as propellants are given in the above-mentioned patents and include trichlorofluoromethane, dichlorodifluoromethane, dichlorotetrafluoroethane, monochlorodifluoromethane, trichlorotrifluoroethane, propane, butane, 1,1-difluoroethane, 1,1-difluoro-1-chloroethane, dichloromonofluoromethane, methylene chloride, isopentane and isobutane, used singly or admixed. Trichlorofluoromethane, dichlorodifluoromethane, dichlorotetrafluoroethane, and isobutane, used singly or admixed, are preferred.

Examples of materials that are suitable for use as permanent gas propellants are nitrogen, carbon dioxide and nitrous oxide.

It is common practice to include in aerosol powder spray compositions a material to assist in the suspending of the powder in the liquid vehicle. The materials prevent compacting of the powder and they may also act as thickening or gelling agents for the liquid vehicle. Especially preferred are hydrophobic clays and colloidal silicas. Hydrophobic clays are available under the trade name Bentone, eg Bentone 34 or Bentone 38, and their use as suspending agents are described in a number of patent specifications including U.S. Pat. No. 3,773,683. Suitable colloidal silicas include Aerosil 200 and Cab-O-Sil M-5 as well as other grades.

The antiperspirant composition may, however, simply comprise from 5 to 40% by weight of said basic aluminium compound in powder form, the remainder consisting essentially of an inert powder material, such as talc or starch, for example.

The invention also relates to a novel polymeric aluminium compound in solid form having the empirical formula

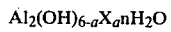

$$Al_2(OH)_{6-a}X_a nH_2O$$

where X is selected from the group consisting of Cl, Br and I, a is from about 0.3 to about 4 and n is from 0.5 to 8, wherein said compound is further characterized by:

(a) having a Size Exclusion Chromatography Test Band having a relative retention time corresponding to Band III of the Standard Basic Aluminium Chloride Solution Size Exclusion Chromatogram; and (b) having a Band III Percent Aluminium Value of at least 20 percent.

A form of said solid compound particularly suitable for use in aerosol powder spray compositions is one comprising particles having a size less than 100 microns, preferably less than 44 microns.

In a further aspect, the invention relates to a novel aqueous solution of a basic aluminium chloride, bromide or iodide having an aluminium to chloride, bromide or iodide molar ratio of from 0.5 to 2.5:1 and having an aluminium content of from 2.5 to 8.5% by weight, the basic aluminium compound being further characterized by:

(a) having a Size Exclusion Chromatography Test Band having a relative retention time corresponding to Band III of the Standard Basic Aluminium Chloride Solution Size Exclusion Chromatogram;

(b) having a Band III Percent Aluminium Value of at least 20 percent; and
(c) less than 2% by weight of the aluminium contained in polymers having an effective diameter greater than 100 Angstroms.

TEST METHODS FOR ASSESSMENT OF EFFICACY OF ANTIPERSPIRANTS

In the Examples given therein five test methods are referred to for the assessment of various antiperspirant active agents referred to therein. Details of the test procedures are described below.

Test Methods I to IV for the assessment of antiperspirant efficacy depend on subjecting human volunteers to thermal stress and gravimetric determination of axillar sweat.

| | Test Method I |
|---|---|
| Subjects | A panel of up to 18 Women who use no antiperspirant for 14 days before the test or during the 16 days interval between the two halves of the test. |
| Hot Room | Temperature 37° C. ± 1° C., relative humidity approximately 35%. |
| Products | Two to four products are tested, one of which is designated as the control. Each subject receives a different treatment on each axilla and as far as possible equal numbers of left and right axillae receive each treatment. |
| Product Application | A two-second spray is administered. |
| Sweat Collection | Absorbent cotton pads are used to collect the sweat. On entering the hot room each subject has a pair of pads placed in her axillae. After 40 minutes these are removed and rejected. Sweat is then collected for two consecutive periods of 20 minutes, fresh tared pads being used for each collection, and sweat weight determined. |
| Test Design | On the first day of the test the subjects receive treatment with the test products but do not undergo a hot room sitting. On each of the next 4 days they undergo hot room sittings, with treatment immediately before each sitting and after showering. The final treatment is omitted on the fifth day. After an interval of 10 days the subjects return and the whole procedure is repeated, with the two products received by each subject applied to the opposite axillae. |
| Analysis of Data | The statistical treatment includes an analysis of variance which allows for subject, side and product effects. The efficacy is calculated from the geometric mean weight of sweat collected from the axillae treated with each product. $$\% \text{ reduction} = 100 \frac{(C - T)}{C}$$ where C is the geometric mean sweat weight from the axillae treated with the control product and T is the geometric mean sweat weight from the axillae treated with the test product. The % reduction is usually calculated for each day separately and for the entire test. Significance is calculated by applying Duncan's Multiple Range Test to the logarithmically transformed weights. |

| | Test Method II |
|---|---|
| Subjects | A panel of up to 54 women who use no antiperspirant for the 14 days before the test. |
| Products | Two aerosol powder spray products of which one is designated the control. The panel is divided into two equal groups. One group receives the test treatment on the left axilla and the control treatment on the right, while the second group receives them the other way round. |
| Test Design | Subjects attend daily for 3 consecutive days. They receive one treatment with the products each days. On the third day the treatment is immediately followed by a hot room sitting and sweat collection. |
| Analysis of Data | As for Test Method I except that significance is calculated by applying Student's t-test to the logarithmically transformed weight. |

The products used in Test Methods I and II had the composition indicated below.

| Ingredient | Test Product I (%) | Test Product II (%) |
|---|---|---|
| Treated or untreated aluminium chlorhydrate | 3.50 | 4.50 |
| Isopropyl myristate | 3.25 | 6.00 |
| Pyrogenic silica (Aerosol 200) | 0.10 | 0.45 |
| Perfume | 0.44 | 0.44 |
| Propellant[1] | to 100.00 | to 100.00 |

[1]$CCl_3F:CCl_2F_2$ - 65:35 by weight (Product I) 50:50 by weight (Product II)

| | Test Method III |
|---|---|
| | As Test Method II with the following differences: |
| Test Product | A solution of treated aluminium chlorhydrate (unless stated otherwise) in water having an aluminium concentration of 2.5% by weight. |
| Control Product | A solution of untreated aluminium chlorhydrate (unless stated otherwise) in water having an aluminium concentration 2.5% by weight. |
| Method of Application | Approximately 0.5 g of solution was applied to each axilla with a cotton swab. |

| | Test Method IV |
|---|---|
| | As Test Method III with the following differences: |
| Method of Application | Approximately 0.5 g of solution was applied to each axilla with a pump-spray applicator. |

Test Method V

This method is the Forearm Starch Iodine Patch Test which was conducted as follows (after Wada & Tokayaki in J. Exp. Med. 49 284 (1948)).

A panel of volunteer test subjects was recruited and each panellist had a number of test solutions applied to separate sites on the volar aspect of the forearm. The solutions (12 drops) were applied under semi-occlusive patches and left for 6 hours. The treatment region of the forearm was then painted with several coats of a 1% solution of iodine in alcohol. After evaporation of the alcohol, the painted area was covered with a 50% suspension of starch powder in oil. The subject was then placed in a heated room (40°±2° C.) until sweating commenced. The effectiveness of the various treatments was then assessed on the basis of the number and size of blue spots arising from the interaction of starch, iodine and sweat.

Determination of water content of powdered materials

The water content of powdered materials was estimated by thermogravimetric analysis (TGA). On heating to 1,000° C., aluminium chlorhydrate undergoes the following reaction:

$$Al_2(OH)_5Cl(H_2O)_x \rightarrow Al_2O_3 + HCl \uparrow + (x+2)H_2O \uparrow$$

From a knowledge of Al/Cl ratio of the material (and hence the empirical weight of the anhydrous $Al_2(OH)_{6-a}Cl_a$) it is possible to calculate the number of moles of water (x) associated with each anhydrous unit from an accurate determination of the weight loss on heating a known weight of sample of 1,000° C. The following equation shows the method of calculation:

$$x = \frac{\left(\frac{\text{Weight of solid before heating}}{\text{Weight of solid after heating}} \times 102\right) - \text{Empirical weight of anhydrous }[Al_2(OH)_{6-a}Cl_a]}{18}$$

The percentage of water is given by $$\frac{1,800x}{\text{Empirical weight of anhydrous }Al_2(OH)_{6-a}Cl_a + 18x}$$

The following Examples illustrate the invention.

EXAMPLE 1

Aluminium chlorhydrate powder having an Al/Cl molar ratio of 2.04 and a water content of 18.5% was dissolved in deionized water so as to give a 10% w/w solution. This solution was heated in 1 liter screw-cap glass bottles to 96° C. over 9 hours and then held at this temperature for a further 39 hours. The resulting solution was cooled to room temperature and found to contain 27.3% of the total aluminium as polymers exceeding 100 Å in effective diameter. The treated solution was spray dried in a co-current spray drier using inlet and outlet temperatures of 250° C. and 95° C., respectively. The resulting powder had an Al/Cl molar ratio of 2.10 and a water content of 14.2%. The powder was sieved to obtain a fraction between 30 and 50 microns.

The spray dried powder was tested for antiperspirant efficacy in two tests using Test Method I.

| | Test No. 1 |
|---|---|
| | This test involved 17 subjects. |
| Test Products | Test Product I made with the treated aluminium chlorhydrate. Two Test Products I made with untreated aluminium chlorhydrate drawn from two different production batches. |
| Control Product | An alcohol-based deodorant. |
| Results | Percent reductions for the products against the control are shown in Table I. "Day 2" refers to the combined results for the second days of each of the 2 weeks, and so on through the table. The table gives the mean of the results for the two products containing untreated aluminium chlorhydrate. |

TABLE I

| Test Product | Day 2 | Day 3 | Day 4 | Day 5 | Overall |
|---|---|---|---|---|---|
| With untreated aluminium chlorhydrate | 7 | 15 | 22 | 22 | 17 |
| With treated aluminium chlorhydrate | 32 | 42 | 47 | 56 | 45 |

The differences between the antiperspirants with treated and untreated aluminium chlorhydrate were significant at the 1% level.

| | Test No. 2 |
|---|---|
| | This was a repetition of Test No. 1 using the same products on 14 different subjects. |
| Results | Percent reductions for the products against the control are shown in Table II where the column headings have the same meanings as before. |

TABLE II

| Test Product | Day 2 | Day 3 | Day 4 | Day 5 | Overall |
|---|---|---|---|---|---|
| With untreated aluminium chlorhydrate | 22 | 16 | 29 | 28 | 24 |
| with treated aluminium chlorhydrate | 34 | 37 | 44 | 44 | 40 |

The differences between the antiperspirants with treated and untreated aluminium chlorhydrate were again significant at the 1% level.

EXAMPLE 2

A batch of Reheis aluminium chlorhydrate Microdry, Ultrafine grade having an Al/Cl molar ratio of 2.04 and a water content of 18.5% was dissolved in deionized water to give a 10% w/w solution. This solution was heated in 1 liter screw-cap glass bottles to 97°–100° C. over 10 hours and then held at this temperature for a further 38 hours. The resulting solution was cooled to room temperature and found to contain 23.9% of the total aluminium as polymers exceeding 100 Å in effective diameter. The solution was tested for antiperspirancy according to Test Method III using a test panel of 46 subjects. The test solution produced a reduction of 22% in the sweat collected compared with the control (10% solution of untreated aluminium chlorhydrate solution), which was statistically significant at the 0.1% level.

The treated solution was then spray dried and the powder sieved as described in Example 1 to give a material with an Al/Cl molar ratio of 2.14 and a water content of 14.3%. The powder was tested according to Test Method II (with 43 panellists) using a suspension-type aerosol antiperspirant of formula according to Test Product I. The product containing the treated aluminium chlorhydrate gave a 25% reduction in sweat compared with the control product containing the untreated aluminium chlorhydrate which was significant at the 0.1% level.

EXAMPLE 3

5.0 kg of Reheis aluminium chlorhydrate having an Al/Cl molar ratio of 2.15 and a water content of 16.1% was dissolved in 45 liters of deionized water at 50°–60° C. in a 50 liter stainless steel reactor internally spray-coated with polytetrafluoroethylene and equipped with a propeller stirrer and partial steam jacket. The solution was stirred and heated to 100° C. in the closed reactor over 10 minutes, then held at this temperature with stirring for 48 hours. After this time the solution was cooled to ambient temperature and homogenised to disperse any gel that may have been formed. The solution contained 43.3% of the total aluminium as polymers greater than 100 Å in effective diameter. When tested for antiperspirancy according to Test Method III with a panel of 19 subjects and using as control the 10% solution of treated aluminium chlorhydrate of Example 2, the test solution produced a reduction of 10% in the sweat collected, the difference being statistically significant at the 10% level.

EXAMPLE 4

5.0 kg of aluminium chlorhydrate (sold as Reheis aluminium chlorhydrate Microdry, Ultrafine grade) having an Al/Cl molar ratio of 2.15 and a water content of 16.1% was dissolved in 45 liters of deionized water at 50°–60° C. in the reactor described in Example 3. The solution was stirred and heated to 120° C. in the closed reactor over 15 minutes, and then held at this temperature with stirring for 6 hours. After this period, the solution was cooled to 90° C. over 15 minutes, then discharged into a holding vessel and allowed to cool to ambient temperature. Before further treatment, the solution was passed through a homogeniser. This solution contained 40.8% of the total aluminium as polymers exceeding 100 Å in effective diameter. When tested for antiperspirancy according to Test Method III with a test panel of 42 subjects and using as control the 10% solution of the treated aluminium chlorhydrate of Example 3, the solution produced a reduction of 1% in the sweat collected. The difference was not statistically significant at the 5% level.

A portion of the treated solution was spray dried by the method described in Example 1. The resulting powder had an Al/Cl ratio of 2.23 and a water content of 11.2%. The powder was sieved to obtain a fraction between 30 and 50 microns which was incorporated into a suspension-type aerosol antiperspirant (Test Product II formula) and compared according to Test Method II (using a panel of 51 subjects) with a once commercially available highly effective powder spray product based on a zirconium/aluminium complex as control and found to give a reduction of 7% in the sweat collected. This was not statistically significant at the 5% level.

When a sample of the spray dried powder was heated for 24 hours at 120° C. the dried product obtained had the empirical formula $Al_2(OH)_{5.31}Cl_{0.69}$. The solution obtained on dissolving this anhydrous powder in water was shown to contain 45.4% by weight of the total aluminium in polymers having an effective diameter of more than 100 Å.

EXAMPLE 5

10 kg of a 50% w/w solution of aluminium chlorhydrate (available commercially as Reheis "Chlorhydrol") which had an Al/Cl molar ratio of 2.09, was added to 40 liters of deionized water and the resulting solution was stirred and heated at 120° C. for 6 hours in the closed reactor as described in Example 3. The treated solution contained 32.9% of the total aluminium as polymers exceeding 100 Å in effective diameter and when compared by Test Method III on a panel of 45 subjects with the 10% solution of treated aluminium chlorhydrate of Example 4 as control gave a 2% increase in the sweat collected but this was not statistically significant at the 5% level.

A portion of the treated solution was concentrated under vacuum in a rotary evaporator at 40° C. to give a solution which was 1.62 molar in aluminium equivalent to 17.1% treated aluminium chlorhydrate.

A further portion of the solution was spray dried by the procedure described in Example 1 to give a powder which had an Al/Cl molar ratio of 2.05 and a water content of 12.7%. A sample of this powder was redissolved in deionized water and was shown to contain 32.4% of the total aluminium as polymers of a size exceeding 100 Å. The powder was sieved to give a 30–50 micron fraction which was formulated into a suspension-type aerosol antiperspirant (Test Product 11). This was compared using Test Method II (involving 48 panellists) with the same powder spray control as used in Example 4 and it gave a 14% reduction in sweat collected which was statistically significant at the 5% level.

EXAMPLE 6

A solution of aluminium chlorhydrate was prepared as described in Example 3 and was stirred and heated to 120° C. in the closed reactor over 15 minutes. Stirring and heating at this temperature was continued and after 1 hour, 6 hours and 25 hours samples of approximately 2 kg of the solution were withdrawn from the reactor, cooled rapidly to room temperature and homogenised. These solutions contained 19.4%, 45.1% and 78.4%, respectively, of their total aluminium as polymers exceeding 100 Å in effective diameter. The results of antiperspirancy tests on these materials by Test Method IV are included in Table III.

EXAMPLE 7

Reheis aluminium chlorhydrate, Microdry, Ultrafine grade having an Al/Cl molar ratio of 1.91 and a water content of 18.8% was dissolved in deionized water to give a 10% w/w solution. This solution was placed in 25 ml Pyrex screw-cap tubes equipped with polytetrafluoroethylene washers and heated to 115° C. in an oil bath for 2 hours. The solutions were cooled to ambient temperature and found to contain 5.3% of the total aluminium as polymers greater than 100 Å in effective diameter. The result of antiperspirancy testing of this solution, by Test Method IV, is shown in Table III.

TABLE III

| Test Solution | % of Total Al as Polymers Greater Than 100 A | Control Solution | % Difference[3] | Significance Level (%) | No. of Subjects | Estimated % Reduction if Tested Against Water |
|---|---|---|---|---|---|---|
| 10% untreated | 0 | water | −20 | 5 | 24 | 20 |

TABLE III-continued

| Test Solution | % of Total Al as Polymers Greater Than 100 Å | Control Solution | % Difference[3] | Significance Level (%) | No. of Subjects | Estimated % Reduction if Tested Against Water |
|---|---|---|---|---|---|---|
| ACH[1] | | | | | | |
| 10% treated ACH | 5.3 | 10% ACH | −8 | 20 | 24 | 26 |
| 10% treated ACH | 19.4 | 10% ACH | −21 | 5 | 22 | 37 |
| 10% treated ACH | 45.1 | 10% ACH | −30 | 5 | 24 | 44 |
| 10% treated ACH | 78.4 | 10% treated ACH[2] | +24 | 5 | 24 | 31 |

[1]ACH = aluminium chlorhydrate.
[2]Product of Example 6 containing 45.1% aluminium as polymers greater than 100 Å.
[3]A minus sign shows that the test solution gave a reduction in sweating compared to the control.

EXAMPLE 8

70 kg of a Reheis aluminium chlorhydrate having an Al/Cl molar ratio of 1.91 and a water content of 18.8% was dissolved in 630 kg of deionized water at 45° C. and stirred and heated to 120° C. in a stainless steel reactor over 3.75 hours. Stirring and heating at this temperature was maintained for a further 5.5 hours before cooling rapidly to 70° C. and more slowly to ambient temperature. The resulting solution contained 41.0% of the total aluminium as polymers exceeding 100 Å in effective diameter.

EXAMPLE 9

140 kg of Reheis "Chlorhydrol" solution having an Al/Cl ratio of 2.09 was diluted with 560 liters of deionized water at 45° C. and treated in a similar manner in the reactor as described for the solution in Example 8. The resulting solution was found to contain 30.6% of the total aluminium as polymers greater than 100 Å in effective diameter.

EXAMPLE 10

30%, 20%, 15% solutions of a Reheis aluminium chlorhydrate having an Al/Cl ratio of 1.91 and a water content of 18.8% were prepared and heated to 120° C. in 25 ml Pyrex glass screw-cap tubes, equipped with polytetrafluoroethylene washers, in a fan oven for 6 hours. The resulting solutions contained 0%, 6.3% and 20.8%, respectively, of the total aluminium as polymers exceeding 100 Å in effective diameter.

EXAMPLE 11

A more basic aluminium chlorhydrate solution was prepared by heating a solution of 36.3 g of aluminium chloride hexahydrate in 150 g of deionized water in the presence of 145 g of 0.5 mm thick aluminium metal sheet, subdivided to approximately 6 mm squares, at 90° C. for 31 hours. After cooling to room temperature the solution was decanted from the excess aluminium and found to have an Al/Cl molar ratio of 2.5 and 0% of the total aluminium as polymeric species exceeding 100 Å in effective diameter. This solution was diluted to an aluminium concentration of 0.95 M and a portion of the diluted solution was heated at 120° C. for 8 hours in 25 ml Pyrex glass screw-cap tubes, fitted with polytetrafluoroethylene washers, in a fan oven. The cooled solution contained 37.6% of the total aluminium as polymeric species exceeding 100 Å in effective diameter and when compared by Test Method IV, on a panel of 20 subjects, with the non-heat-treated diluted solution as control, gave a 36% decrease in the sweat collected which was significant at the 0.1% level.

EXAMPLE 12

A 10% w/w solution of a basic aluminium bromide having an Al/Br molar ratio of 2 and a water content of about 22% was prepared and heated to 100° C. in a 1 liter screw-cap glass bottle for 62 hours in a fan oven. The resulting solution was immediately cooled to room temperature and found to contain 46.4% of the total aluminium as polymers exceeding 100 Å in effective diameter. When tested for antiperspirancy using Test Method V this solution was found to be appreciably more effective than an untreated solution of the basic aluminium bromide at the same concentration.

COMPARATIVE EXAMPLE A

A 50% w/w solution of a Reheis aluminium chlorhydrate having an Al/Cl molar ratio of 1.91 and a water content of 18.8% was prepared and heated to 120° C. in 25 ml Pyrex glass screw-cap tubes, equipped with polytetrafluoroethylene washers, in a fan oven for 24 hours. The resulting solution contained 0% of the aluminium in polymers exceeding 100 Å in effective diameter. When tested for antiperspirancy as a 10% w/w solution according to Test Method IV, on a panel of 46 subjects, this solution gave 2% increase in the sweat collected compared to an untreated solution of aluminium chlorhydrate of the same concentration. This result was not statistically significant at the 5% level.

COMPARATIVE EXAMPLE B

An aqueous solution of an aluminium chlorhydrate having an aluminium concentration of 10.0% by weight and an Al/Cl molar ratio of 2.00 was placed in a 25 ml Pyrex glass tube equipped with a screw-cap and a polytetrafluoroethylene washer and heated at 120° C. for 24 hours. After cooling to room temperature, the solution was analysed and found to contain 0% of the total aluminium in polymers exceeding 100 Angstroms in effective diameter and 18% of the aluminium in the Band III fraction.

The Band III Percent Aluminium Values for the treated products obtained in accordance with the above Examples are given below in Table IV.

TABLE IV

| Example | Band III Percent Aluminium Value |
|---|---|
| 1 | 30 |
| 2 | 43 |
| 3 | 27 |
| 4 | 26 |
| 5 | 30 |
| 6 (i) 1 hour heating | 39 |
| (ii) 6 hour heating | 32 |
| (iii) 25 hour heating | 5 |
| 7 | 36 |
| 8 | 26 |
| 9 | 29 |
| 10 (i) 30% solution | 26 |
| (ii) 20% solution | 47 |
| 12 (iii) 15% solution | 56 |
| 11 | 43 |
| 12 | 29 |
| Comparative Example A | 9 |
| Comparative B | 18 |

EXAMPLE 13

28 kg of a 50% w/w solution of aluminium chlorhydrate which had an Al/Cl molar ratio of 1.99, was added to 42 kg of deionised water in a 75 liter stainless steel reactor internally spray coated with polytetrafluoroethylene and equipped with a propeller stirrer and partial steam jacket. The solution was stirred and heated to 120° C. in the closed reactor over a period of 1 hour, then held at this temperature for 4 hours. The treated solution was spray dried in a co-current spray drier using inlet and outlet temperatures of 250° C. and 90° C., respectively. The powder was sieved to remove particles greater than 74 microns and tested according to Test Method II with Test Product II (with 26 panellists). The product containing the treated aluminium chlorhydrate gave a 25% reduction in sweat compared with the control product containing a commercially available aluminium chlorhydrate powder ("Microdry Ultrafine"). The result was statistically significant at the 0.1% level. When tested by the chromatographic methods, a solution from the redissolved powder was found to contain 1% of the total aluminium as polymers greater than 100 Angstroms in effective diameter and 30% of the total aluminium in the Band III fraction.

EXAMPLE 14

23.9 kg of a 50% w/w solution of aluminium chlorhydrate which had an Al/Cl molar ratio of 1.99 was added to 36.0 kg of deionised water at ambient temperature in the reactor described in Example 1. 110.2 g of aluminium chloride hexahydrate was added and the solution stirred to effect complete dissolution. The Al/Cl molar ratio in the final solution was 1.95. The solution was then heated to 120° C. in the closed reactor over a period of 1 hour and held at this temperature for 10 hours before cooling to ambient temperature in 1 hour. The treated solution was spray dried in a co-current spray drier using inlet and outlet temperatures of 250° C. and 90° C., respectively. The powder was sieved to remove particles greater than 74 microns and tested according to Test Method II with Test Product II (with 40 panellists). The product containing the treated aluminium chlorhydrate gave an 18% reduction in sweat compared with the control product as in Example 13. The result was statistically significant at the 0.1% level. Upon testing the redissolved powder according to the chromatographic methods, the solution was found to contain 0% of the total aluminium as polymers greater than 100 Angstroms in effective diameter and 37% of the total aluminium in the Band III fraction.

EXAMPLE 15

95 g of aluminium chlorhydrate powder having an Al/Cl molar ratio of 2.00 and a water content of 17.1% was mixed with 11.5 g of aluminium chloride hexahydrate and dissolved in deionised water, to give 1 kg of solution. The Al/Cl ratio in the final solution was 1.60. Samples of this solution were placed in 25 ml Pyrex glass screw-cap tubes equipped with polytetrafluoroethylene gaskets and heated to 116° C. for 20 hours. The solution was cooled to ambient temperature and found to contain 0% of the total aluminium in polymers greater than 100 Angstroms in effective diameter and 50% of the total aluminium in the Band III fraction. When the treated solution was tested for antiperspirancy against the untreated solution was control according to Test Method IV (using a panel of 24 subjects) a reduction of 13% in the sweat collected was observed. The difference was statistically significant at the 5% level. In another test using Test Method IV (on a panel of 24 subjects) and a 10% solution of the aluminium chlorhydrate as control, the treated solution gave a reduction of 16% in the sweat collected. The difference was statistically significant at the 2% level.

EXAMPLE 16

200 g of a 50% w/w solution of aluminium chlorhydrate which had an Al/Cl ratio of 1.99 was added to 800 g of deionised water. Samples of this solution were placed in 25 ml Pyrex glass screw-cap tubes equipped with polytetrafluoroethylene gaskets and maintained at 50° C. for 14 days. The solution was cooled to room temperature and found to contain 0% of the total aluminium in polymers greater than 100 Angstroms in effective diameter and 24% of the total aluminium in the Band III fraction.

EXAMPLE 17

A commercially available basic aluminium chloride solution having a molar ratio of 1.30 was diluted with deionized water to an aluminium concentration of 2.5% by weight. Samples of this solution were placed in 25 ml Pyrex glass screw-cap tubes equipped with polytetrafluoroethylene washers heated to 120° C. for 16 hours, and cooled to ambient temperature. The treated solution was found to contain 0.0% of the total aluminium in polymers greater than 100 A in effective diameter and 65% of the aluminium in the Band III fraction.

The treated solution was tested according to Test Method IV (using a panel of 42 subjects) employing a control solution prepared by dilution of the same commercial basic aluminium chloride solution referred to above and which contained 0% of the total aluminium in polymers greater than 100 Angstroms in effective diameter and 17% of the aluminium in the Band III fraction. Both test products were freshly prepared for each day of the antiperspirant test. The treated solution gave a reduction of 19% in the sweat collected compared with the control product. This was statistically significant at the 5% level.

EXAMPLE 18

Stock solutions were prepared from a 50% by weight aluminium chlorhydrate solution having an aluminium concentration of 12.27% by weight and an Al/Cl molar ratio of 1.97, and aluminium chloride hexahydrate, or a soluble aluminium hydroxide which was 47.0% $Al_2O_3$ by weight, as appropriate, and deionized water. Solutions were prepared at 10.0% aluminium concentration by weight and Al/Cl ratios ranging from 0.9 to 2.2. Ratios lower than 0.9 were prepared at the concentrations required. Heating to a maximum of 40° C. with stirring was employed to assist dissolution of the aluminium hydroxide.

Samples were prepared from the stock solutions and deionized water in 25 ml Pyrex glass tubes equipped with screw-caps and polytetrafluoroethylene washers. The tubes were heated in a fan oven for the designated time plus 30 minutes to allow for equilibration of the temperature. At the end of the heating period, the tubes were removed from the oven and cooled rapidly to room temperature in flowing water. The treated samples were analysed immediately for their Band III fraction by the chromatographic procedures described herein. Results of experiments involving reaction times of 24 hours and 6 hours are indicated below in Tables V and VI, respectively. In certain places in the tables two values are given, e.g. 77/6. The first value is the percentage of aluminium in the Band III fraction and the second figure is the percentage of aluminium in polymers exceeding 100 Angstroms. Where only one value is given this is the percentage of aluminium in the Band III fraction, the amount of aluminium in polymers exceeding 100 Angstroms in these cases being 0%.

TABLE V

| Al/Cl molar ratio | 60° C. 2.5% | 60° C. 5.0% | 60° C. 7.5% | 100° C. 2.5% | 100° C. 5.0% | 100° C. 7.5% | 120° C. 2.5% | 120° C. 5.0% | 120° C. 7.5% |
|---|---|---|---|---|---|---|---|---|---|
| | wt % Al | | | | | | | | |
| 0.7 | 15 | 8 | | 22 | | | | | |
| 0.8 | | | | | | | | 12 | |
| 0.9 | 23 | | | | 12 | | | | |
| 1.2 | 35 | 13 | | 58 | | | 63 | 22 | |
| 1.5 | | | | | 39 | 15 | 75 | | 16 |
| 1.7 | | | | | | | 77/6 | | |
| 1.8 | | 26 | | 79 | | | | 57/1 | 29 |
| 1.9 | | | | | | | | | |
| 2.0 | | | | | 40 | | | | |
| 2.1 | | 15 | 10 | 62/24 | 42/10 | 21 | | | |
| 2.2 | | 12 | | | | | | | 24/43 |

TABLE VI

| Al/Cl molar ratio | TEMPERATURE OF 120° C. | | |
|---|---|---|---|
| | wt % Al | | |
| | 2.5% | 5.0% | 7.5% |
| 0.7 | 23 | 9 | |
| 0.8 | | | |
| 0.9 | | | 10 |
| 1.2 | | 23 | |
| 1.5 | 78 | | 23 |
| 1.7 | 81 | | |
| 1.8 | 80/1 | | |
| 1.9 | | 53 | |
| 2.0 | | 50/2 | |
| 2.1 | | | 31/8 |
| 2.2 | | | |

The above tables indicate the influence of reaction temperature, Al/Cl molar ratio, and concentration on the production of polymers in the Band III fraction.

For a given Al/Cl molar ratio, reaction temperature and reaction time, the Band III value decreases with increasing concentration. For a given temperature, time and concentration, the Band III value increases to a maximum and then decreases with increasing Al/Cl molar ratio. For a given Al/Cl molar ratio, time and concentration, the Band III value increases with increase in temperature. The tables also show how the temperature and concentration affect the production of polymers exceeding 100 Angstroms in size in relation to the Al/Cl molar ratio.

From numerous experiments that Applicants have conducted including those in the above tables equations have been derived for expressing the percentage aluminium in the Band III fraction resulting from heat treating particular basic aluminium chlorides under certain reaction conditions. Thus for reactions involving compounds having an Al/Cl molar ratio of from 0.6 to 2.2 at temperatures of from 60° to 120° C. and aluminium concentrations from 5.0 to 7.5%, and also for the reaction at 60° C. and an aluminium concentration of 2.5%, the Band III percentage aluminium value is given by the expression:

% Band III Al = 9.-
29A − 19.17B + 5.10C + 3.49D − 6.01  AD + 1.28
AC − 1.80BC − 2.30 CD − 11.55 $C^2$ − 3.89 $A^2$ + 1.89
$B^2$ − 1.94  $D^2$ + 1.64  ABD − 5.58  ACD + 0.56
BCD − 5.34  $AC^2$ + 6.38  $BC^2$ − 2.33  $C^2D$ + 3.94
$C^3$ + 2.87  $A^2B$ − 5.52  $A^2D$ − 3.19  $A^2C$ + 0.90
$BD^2$ − 2.17 $AD^2$ − 1.88 $CD^2$ − 0.86 $B^2C$ + 41.9 where A, B, C and D are as follows:

$$A = \frac{T - 100}{25} \qquad B = \frac{[Al] - 5.5}{1.5}$$

$$C = \frac{e^{2R} - 37.5}{26} \qquad D = \frac{t - 19.0}{17.0}$$

where T is the reaction temperature in degrees Centigrade [Al] is the concentration expressed in percent aluminium by weight R is the Al/Cl molar ratio t is the time in hours at temperature T.

For reactions at 100°–120° C. and at an aluminium concentration of 2.5%, the corresponding expression for compounds having an Al/Cl molar ratio in the range of 0.6 to 2.2, is:

% Band III Al = −5.28 $A_1$ − 9.58 $B_1$ − 1.08 $C_1$ − 8.73
$A_1C_1$ − 1.98  $A_1B_1$ = 5.44  $B_1C_1$ − 5.97
$A_1B_1C_1$ − 22.92 $B_1^2$ − 1.82 $B_1^2C_1$ + 7.40 $B_1^3$ + 5.84
$A_1C_1^2$ + 76.2 where $A_1$, $B_1$ and $C_1$ are as follows:

$$A_1 = \frac{T - 113}{9.5} \qquad C_1 = \frac{t - 11.0}{9.0}$$

$$B_1 = \frac{e^R - 5.5}{2.5}$$

The following Examples 19 to 29 are of various formulations which may be made from the treated basic aluminium compounds described in the preceding Examples. Percentages are by weight. For the sake of simplicity the treated aluminium antiperspirant in powder and solution form are referred to herein as "treated powder" and "treated solution", respectively.

Examples 19 to 24 are of powder aerosol spray compositions of the suspension type which are employed with an aerosol application.

EXAMPLE 19

|  | % |
|---|---|
| Treated powder | 3.50 |
| Isopropyl myristate | 3.50 |
| Aerosil 200 (pyrogentic silica) | 0.10 |
| Perfume | 0.44 |
| Propellant[1] | q.s. 100.00 |

[1]$CCl_3F:CCl_2$ 65:35 by weight

EXAMPLE 20

|  | % |
|---|---|
| Treated powder | 4.50 |
| Isopropyl myristate | 6.00 |
| Aerosil 200 (pyrogenic silica) | 0.45 |
| Perfume | 0.44 |
| Propellant[1] | q.s. 100.00 |

[1]Propellant $CCl_3F:CCl_2F_2$ 50:50 by weight

EXAMPLE 21

|  | % |
|---|---|
| Treated powder | 3.50 |
| Isopropyl myristate | 8.00 |
| Bentone 38 (hydrophobic clay) | 0.60 |
| Ethyl alcohol (95%) | 0.27 |
| Perfume | 0.40 |
| Propellant[1] | q.s. 100.00 |

[1]Propellant $CCl_3F:CCl_2F_2:CClF_2—CClF_2$:n-butane 20:10:50:20 by weight

EXAMPLE 22

|  | % |
|---|---|
| Treated powder | 3.50 |
| Dibutyl phthalate | 8.00 |
| Stearoyl monoethanlamide | 0.60 |
| Perfume | 0.40 |
| Propellant[1] | q.s. 100.00 |

[1]Propellant $CCl_3F:CCl_2F_2$:butane 40:30:30 by weight

EXAMPLE 23

|  | % |
|---|---|
| Treated powder | 4.00 |
| Isopropyl myristate | 6.00 |
| Methylene chloride | 25.00 |
| 1:1:1 trichloroethane | 5.00 |
| Aerosil 200 (pyrogenic silica) | 0.45 |
| Butane 40 | 59.55 |

EXAMPLE 24

|  | % |
|---|---|
| Treated powder | 4.00 |
| Bentone 38 (hydrophobic clay) | 0.40 |
| Isopropyl myristate | 6.00 |
| Perfume | 0.50 |
| Propellant 142b | 89.10 |

EXAMPLE 25

The following is an example of an antiperspirant lotion suitable for use with a roll-on applicator.

|  | % |
|---|---|
| Treated powder | 5.00 |
| Urea | 5.00 |
| Ethanol | 50.00 |
| Water | 35.00 |
| Tween 80 (polyoxyethylene sorbitan monooleate) | 5.00 |

EXAMPLE 26

The following is an example of an antiperspirant lotion suitable for use with a roll-on applicator.

|  | % |
|---|---|
| Treated solution (3.13 wt % Al) | 80.00 |
| Glyceryl monostearate (Arlacel 165) | 10.00 |
| Distilled water | 10.00 |

EXAMPLE 27

The following is an example of an antiperspirant lotion suitable for use with a roll-on or pump spray applicator.

|  | % |
|---|---|
| Treated powder | 12.50 |
| Ethanol | 30.00 |
| Glycine | 5.00 |
| Tween 20 (polyoxyethylene sorbitan monolaurate) | 2.50 |
| water | 50.00 |

EXAMPLE 28

The following is an example of a formula for a composition in the form of a stick for use with a stick applicator.

|  | % |
|---|---|
| Treated powder | 20.00 |
| Volatile silicone 7158[1] (Union Carbide) | 48.00 |
| Span 85 (sorbitan trioleate) | 2.00 |
| Ceto-stearyl alcohol | 30.00 |

[1]Decamethylcyclopentasiloxane

EXAMPLE 29

The following is an example of an antiperspirant cream composition.

|  | % |
|---|---|
| Treated solution (4.38 wt % Al) | 85.70 |
| Glyceryl monostearate (Arlacel 165) | 10.00 |
| Water | 4.30 |

What is claimed is:

1. Process for improving the antiperspirant activity of a basic aluminum compound consisting essentially of a complex having the empirical formula:

where X is Cl, Br or I, and a is about 0.3 to about 4, comprising the steps of:
(i) heating an aqueous liquid solution containing the basic aluminum compound at an aluminum concentration of 2.5 to 8.5% by weight of the solution at a temperature of 50° to 140° C. for a period of time sufficient to impart to said basic aluminum compound the property of:
 (a) having a Size Exclusion Chromatography Test Band having a relative retention time corresponding to Band III of the Standard Basic Aluminum Chloride Solution Size Exclusion Chromatogram; and
 (b) having a Band III Percent Aluminum Value of at least 20 percent; and
(ii) cooling the aqueous liquid to ambient temperature;

thereby obtaining an aqueous liquid solution containing a basic aluminum compound having substantially the same empirical formula as the basic aluminum compound in the aqueous liquid solution prior to said heating and having enhanced anti-perspirant activity.

2. Process for improving the antiperspirant activity of a basic aluminum compound consisting essentially of a complex having the empirical formula:

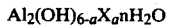

where X is Cl, Br or I, and a is about 0.3 to about 4, and n is about 0.5 to about 8, comprising the steps of:
(i) heating an aqueous liquid solution containing the basic aluminum compound at an aluminum concentration of 2.5 to 8.5% by weight of the solution at a temperature of 50° to 140° C. for a period of time sufficient to impart to said basic aluminum compound the property of:
 (a) having a Size Exclusion Chromatography Test Band having a relative retention time corresponding to Band III of the Standard Basic Aluminum Chloride Solution Size Exclusion Chromatogram; and
 (b) having a Band III Percent Aluminum Value of at least 20 percent; and
(ii) drying the aqueous liquid to give a basic aluminum compound having enhanced anti-perspirant activity and substantially the same empirical formula as the basic aluminum compound in the aqueous liquid solution prior to said heating in the form of a hydrated water-soluble powder retaining the property of:
 (a) having a Size Exclusion Chromatography Test Band having a relative retention time corresponding to Band III of the Standard Basic Aluminum Chloride Solution size Exclusion Chromatogram; and
 (b) having a Band III Percent Aluminum Value of at least 20 percent.

3. Process as claimed in claims 1 or 2 wherein the solution is heated for a period of 0.5 hours to 30 days.

4. Process as claimed in claims 1 or 2 wherein the Band III Percent Aluminum Value of the basic aluminum compound is at least 25 percent.

5. Process as claimed in claims 1 or 2 wherein the basic aluminum compound is further characterized by:
 (c) having at least 2% of the aluminum contained in polymeric species having an effective diameter greater than 100 Angstroms.

6. Process as claimed in claims 1 or 2 wherein the basic aluminum compound is further characterized by:
 (c) having less than 2% of the aluminum contained in polymeric species having an effective diameter greater than 100 Angstroms.

7. Process as claimed in claims 1 or 2 wherein the basic aluminum compound has an aluminum to chloride, bromide or iodide molar ratio of from 0.5 to 2.5:1.

8. Process as claimed in claims 1 or 2 wherein heating step (ii) effects an increase in the Band III Percent Aluminum Value of at least 10 percentage units.

9. Process as claimed in claims 1 or 2 wherein said heating increases the Band III percent aluminum value by at least 10 percentage units.

* * * * *

UNITED STATES PATENT AND TRADEMARK OFFICE
CERTIFICATE OF CORRECTION

PATENT NO. : 4,359,456

DATED : November 16, 1982

INVENTOR(S) : Gosling et al

It is certified that error appears in the above—identified patent and that said Letters Patent is hereby corrected as shown below:

On the title page:

Item [63], line 1, delete "Ser. No. 51,523" and add -- Ser. No. 51,583 --.

Column 1, line 5, delete "Ser. No. 51,523" and insert -- Ser. No. 51,583 --.

Signed and Sealed this

Twenty-second Day of March 1983

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,359,456

DATED : November 16, 1982

INVENTOR(S) : Gosling, et al.

It is certified that error appears in the above-identified patent and that said Letters Patent are hereby corrected as shown below:

Change Column 22, lines 23 through 29 from the following:

"% Band III Al=9.
29A-19.17B+5.10C+3.49D-6.01 AD+1.28
AC-1.80BC-2.30CD-11.55$C^2$-3.89$A^2$+1.89
$B^2$—1.94 $D^2$+1.64 ABD—5.58 ACD+0.56
BCD—5.34 $AC^2$+6.38 $BC^2$—2.33 $C^2$D+3.94
$C^3$+2.87 $A^2$B—5.52 $A^2$D —3.19 $A^2$C+0.90
$BD^2$—2.17 $AD^2$—1.88 $CD^2$—0.86 $B^2$C+41.9 to read as the following

--% Band III Al = 9.29A - 19.17B + 5.10C + 3.49D
- 6.01 AD + 1.28 AC - 1.80BC - 2.30 CD - 11.55 $C^2$
- 3.89 $A^2$ + 1.89 $B^2$ - 1.94 $D^2$ + 1.64 ABD - 5.58 ACD
+ 0.56 BCD - 5.34 $AC^2$ + 6.38 $BC^2$ - 2.33 $C^2$D + 3.94 $C^3$
+ 2.87 $A^2$B - 5.52 $A^2$D - 3.19 $A^2$C + 0.90 $BD^2$ - 2.17 $AD^2$
- 1.88 $CD^2$ - 0.86 $B^2$C + 41.9--

UNITED STATES PATENT AND TRADEMARK OFFICE
CERTIFICATE OF CORRECTION

PATENT NO. : 4,359,456  Page 2 of 2
DATED : November 16, 1982
INVENTOR(S) : Gosling, et al.

It is certified that error appears in the above-identified patent and that said Letters Patent are hereby corrected as shown below:

Change column 22, lines 47 through 50 from the following:

"% Band III Al=—5.28 $A_1$ —9.58 $B_1$ — 1.08 $C_1$ — 8.73 $A_1C_1$ —1.98 $A_1B_1$ =5.44 $B_1C_1$ — 5.97 $A_1B_1C_1$ —22.92 $B_1^2$ —1.82 $B_1^2C_1$ +7.40 $B_1^3$ + 5.84 $A_1C_1^2$ +76.2 to read as follows:

--% Band III Al = — 5.28 $A_1$ — 9.58 $B_1$ — 1.08 $C_1$ - 8.73 $A_1C_1$ - 1.98 $A_1B_1$ - 5.44 $B_1C_1$ — 5.97 $A_1B_1C_1$ - 22.92 $B_1^2$ - 1.82 $B_1^2C_1$ + 7.40 $B_1^3$ + 5.84 $A_1C_1^2$ + 76.2 --

Signed and Sealed this

Tenth Day of January 1984

[SEAL]

Attest:

GERALD J. MOSSINGHOFF

Attesting Officer  Commissioner of Patents and Trademarks